(12) United States Patent
Carlino

(10) Patent No.: US 7,939,655 B2
(45) Date of Patent: May 10, 2011

(54) PROCESS FOR PREPARING A STERILE HIGH MOLECULAR WEIGHT HYALURONIC ACID FORMULATION

(75) Inventor: Stefano Carlino, Monthey (CH)

(73) Assignee: Laboratoire Medidom S.A., Geneva (CH)

( * ) Notice: Subject to any disclaimer, the term of this patent is extended or adjusted under 35 U.S.C. 154(b) by 596 days.

(21) Appl. No.: 10/523,657

(22) PCT Filed: Aug. 4, 2003

(86) PCT No.: PCT/IB03/03524
§ 371 (c)(1),
(2), (4) Date: Feb. 4, 2005

(87) PCT Pub. No.: WO2004/014399
PCT Pub. Date: Feb. 19, 2004

(65) Prior Publication Data
US 2006/0052336 A1    Mar. 9, 2006

(30) Foreign Application Priority Data
Aug. 7, 2002  (EP) .................... 02405681

(51) Int. Cl.
*C07H 5/04* (2006.01)
*C07H 5/06* (2006.01)
(52) U.S. Cl. .................. 536/55.3; 536/55.1
(58) Field of Classification Search .......... 514/54; 62/532
See application file for complete search history.

(56) References Cited

U.S. PATENT DOCUMENTS

| 4,141,973 A | 2/1979 | Balazs |
| 5,093,487 A | 3/1992 | Brown et al. |
| 5,503,848 A * | 4/1996 | Perbellini et al. ............. 424/488 |
| 6,489,467 B1 * | 12/2002 | Carlino et al. ............... 536/55.3 |
| 2002/0120132 A1 | 8/2002 | Prescott |

FOREIGN PATENT DOCUMENTS

| EP | 0631799 A1 * | 4/1995 |
| EP | 0 867 453 A1 | 9/1998 |
| EP | 1 217 008 A1 | 6/2002 |
| WO | WO 93/20858 | 10/1993 |
| WO | WO 00 44925 A | 8/2000 |

OTHER PUBLICATIONS

XP-002262433, Feb. 16, 1990, Showa Sangyo Co.

* cited by examiner

*Primary Examiner* — Elli Peselev
(74) *Attorney, Agent, or Firm* — Krieg DeVault LLP; Clifford W. Browning

(57) ABSTRACT

A process for preparing a sterile ready-to-use aqueous pharmaceutical formulation comprises a high molecular weight hyaluronic acid salt (HA) at a specified concentration, comprising the steps of: providing an aqueous formulation comprising high molecular weight HA at a concentration of less than the specified final concentration; passing said aqueous formulation through a filter having a pore sizeless than 0.45 pm; concentrating said aqueous formulation by applying a vacuum and boiling off water until said specified concentration is reached.

7 Claims, 4 Drawing Sheets

Figure 1:
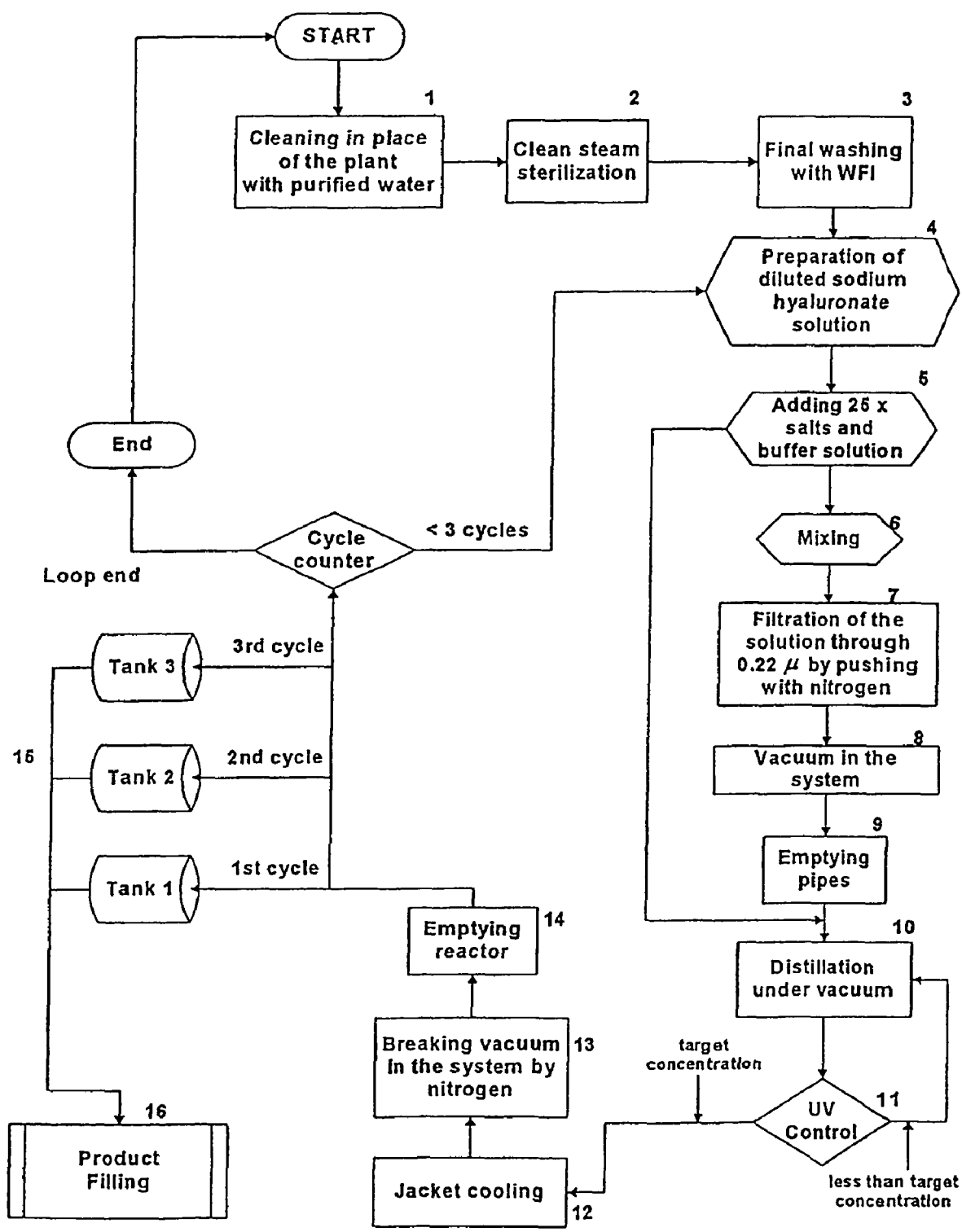

PROCESS FOR PREPARING A STERILE HIGH MOLECULAR WEIGHT HYALURONIC ACID FORMULATION

Applicant claims foreign priority benefits under 35 U.S.C. §§119(a)-(d) or (f), or §365(b) of European Patent Application No. 02405681.4, filed Aug. 7, 2002.

The present invention relates to a process for preparing a sterile high molecular weight hyaluronic acid salt as a final formulation for pharmaceutical use.

Hyaluronic acid in its salt form may for instance include sodium hyaluronate, potassium hyaluronate, magnesium hyaluronate, calcium hyaluronate, or others.

Hyaluronic acid is a mucoid polysaccharide of biological origin, which is widely distributed in nature. For example, it is known that hyaluronic acid is present in various animal tissues such as umbilical cord, synovial fluid, vitreous humor, rooster comb and various connective tissues such as skin and cartilage.

Chemically, hyaluronic acid is a member of glycosaminoglycans and it is constituted by alternating and repeating units of D-glucuronic acid and N-acetyl-D-glucosamine, to form a linear chain having a molecular weight up to $13 \times 10^6$ Daltons.

In the meaning of the present invention, high molecular weight hyaluronic acid is hyaluronic acid having an average molecular weight of not less than $0.5 \times 10^6$ Daltons.

Pharmaceutical use of hyaluronic acid or of a salt thereof is widely described in the literature.

Since hyaluronic acid is a non-immunogenic substance and has viscoelastic and hydrophilic properties, it is used, since several years, as an eye vitreous or joint fluid replacement or as a supportive medium in ophthalmic surgery, as disclosed for example in U.S. Pat. No. 4,141,973 of Balazs.

In joint fluids, the viscous hyaluronic acid solution serves as a lubricant to provide a protective environment to the cells, and for this reason, it is used in the treatment of inflamed knee joints.

EP-A-0 781 547 discloses a sodium hyaluronate based ophthalmic formulation for use in eye surgery.

EP-A-0 719 559 discloses sodium hyaluronate viscous solutions for use as masking fluid in therapeutic photokeratectomy by means of excimer laser.

EP-A-0 875 248 discloses the use of hyaluronic acid or of one of its pharmaceutically acceptable salts for the preparation of an aqueous solution useful as intra-articular lavage liquid.

EP-A-0 698 388 of Chemedica S. A. discloses an ophthalmic preparation for use as artificial tears containing hyaluronate as a viscosity thickener.

The pharmaceutical use of hyaluronic acid or of a salt thereof requires a highly pure and sterile product.

Hyaluronic acid can be extracted and purified from animal or microbial sources such as umbilical cords, rooster combs or from group A and C Streptococci as disclosed for example in U.S. Pat. No. 4,141,973 of Balazs, U.S. Pat. No. 5,559,104 of Romeo et al. and WO 00/4925.

Industrial extraction and purification processus of hyaluronic acid typically produce hyaluronic acid salts, such as sodium hyaluronate, in the form of a dried powder. The purified pharmaceutical grade dried power may be used for preparing, for example, aqueous pharmaceutical formulations for the various pharmaceutical uses such as interarticular injection, eye drops or vitreous humor replacement.

A common industrial process for preparing ready-to-use pharmaceutical formulations comprises the mixing of a defined quantity in weight of sodium hyaluronate with a precise volume of water and, as the case may be, salt such as sodium chloride and buffers such as phosphates and other excipients. As the concentration and composition of the formulation for pharmaceutical use should remain within a narrowly defined range, the various components of the formulation are carefully measured. The formulation is then filled into recipients such as syringes and vials of defined dosages ready for use. Subsequent to filling of the recipients, the formulation is sterilized by autoclave typically at around 121° C. for fifteen minutes or more.

One of the problems with the use of heat to sterilize hyaluronic acid is the known effect on breaking the molecular chains forming HA, thus reducing the average molecular weight of HA.

The high molecular weight of hyaluronic acid is an important pharmacological property.

In many pharmaceutical applications it is undesirable to have low molecular weight hyaluronic acid in the formulation, for example in view of the inflammatory effects of low molecular weight HA as reported in U.S. Pat. No. 4,141,973 and the loss of beneficial reological properties of high molecular weight HA. In order to compensate for degradation of the HA in a formulation of given concentration in the aforementioned sterilization methods, the hyaluronic acid or salts thereof initially used in preparing the formulation have an average molecular weight that is higher than that of the desired minimum average molecular weight of the final formulation. This is however uneconomical since the yield of hyaluronic acid from starting material decreases as the average molecular weight required increases.

Another known method of sterilizing hyaluronic acid is by filtration. This technique is used in conventional industrial processes for preparing purified hyaluronic acid salts in a concentrated form, usually in the form of dried powder, whereby a low concentration aqueous solution is passed through the filter and subsequently dried.

Such sterilization steps are for example described in European patent application EP 867453 and in PCT application WO 00/44925. In these applications, a filter with a pore size as small as 0.22 µm is also disclosed for sterilization. Filters having a pore size of 0.22 µm have a bacterial challenge of 1 over $10^7$ bacteria, based on the smallest known bacterium *Pseudomonas diminuta*, while filters having a pore size of 0.45 µm have a bacterial challenge of 1 over $10^4$ bacteria (always based on *Pseudomonas diminuta*). For this reason, filters having a pore size less than 0.45 µm are considered to be sterilizing.

In conventional industrial processus, the method of sterilization by filtration is not known to be used for preparing high viscosity pharmaceutical formulations ready for use, since at the required concentration of HA in high viscosity pharmaceutical aqueous formulations, typically in the range of 1 to 2% wt/v, not all of the hyaluronic acid passes through the filter at 0.22 µm. Since this results in a change in the concentration and/or a loss of hyaluronic acid, sterilization by filtration for preparing ready-to-use high viscosity pharmaceutical formulations is problematic.

In U.S. Pat. No. 5,093,487, the preparation of an aqueous pharmaceutical formulation comprising high molecular weight sodium hyaluronate ready for use and sterilized through a filter of 0.22 µm is described. The sterilizing method described in this patent however relies on a number of passes of hyaluronic acid aqueous formulation through the 0.22 µm filter, so as to irreversibly reduce the viscosity of the hyaluronic acid. The sterilization of an aqueous pharmaceutical formulation comprising HA at a concentration of 1% or more is, according to this publication, possible in view of the reduction of viscosity of the hyaluronic acid resulting from the multiple passes through the filter. It is further argued in this application that the viscosity is reduced without reducing the molecular weight of HA. Without wishing to take position on the validity of the findings reported in the aforementioned publication, for many pharmaceutical applications such as intra-articular applications, the lowering of the viscosity of HA is undesirable.

An object of the present invention is to obtain a sterile ready-to-use pharmaceutical aqueous formulation comprising a hyaluronic acid salt, that is sterile and economical to produce, particularly in industrial conditions. It is advantageous to provide such formulation with a narrow tolerance in the concentration of the ingredients of the formulation.

Objects of this invention have been achieved by a process for preparing a sterile high molecular weight hyaluronic acid formulation for pharmaceutical use according to claim 1.

Disclosed herein is a process for preparing a sterile ready-to-use aqueous pharmaceutical formulation comprising a high molecular weight hyaluronic acid salt (HA) at a specified final concentration, comprising the steps of:

providing an aqueous formulation comprising high molecular weight HA at a concentration less than the specified final concentration;

passing said aqueous formulation through a filter having a pore size less than 0.45 μm;

concentrating said aqueous formulation by applying a vacuum and boiling off water until said specified final concentration is reached.

Advantageously, the reduced concentration of the aqueous formulation prior to filtering, as a function of the molecular weight, reduces the viscosity and enables the entire HA to pass through the filter and be sterilized, the subsequent boiling with a vacuum ensuring that essentially no heat dependent degradation of HA occurs. The process is well adapted to an industrial environment and is particularly economical, allowing ready-to-use dosages of pharmaceutical formulation comprising HA to be filled in sterile recipients without further sterilization.

A further advantage is that the formulation is microbiologically stable and may be kept for weeks before being used as pharmaceutical preparation.

Viscosity of HA in aqueous solution is a property that depends on several parameters such as molecular weight, concentration, temperature, concentration and quality of salts, pH and shear rate applied to the solution. Higher molecular weight and concentration increase the viscosity, while higher shear rate and salts decrease the viscosity. Regarding the temperature, HA has a hysteretic behavior as reported by M. Cardones et al. "*Hysteresis Behavior of Sodium Hyaluronate Solutions during Heating and Cooling*", Clear Solutions Biotech, Inc., Technical Rep 01. Viscosity increases and decreases in an irregular way by increasing or decreasing the temperature. Between 60° C. and 70° C. it is possible to get the minimum viscosity of the solution. Therefore, this hysteretic property can be used for decreasing or increasing the viscosity of the solution, but it has to be considered that the HA chains degradation is proportional to the temperature and the duration at which this temperature is kept.

During the concentrating step after filtration, the concentration of HA may be monitored in real time in order to stop the vacuum boiling when the specified concentration for the ready-to-use pharmaceutical formulation is reached. The monitoring or measuring process may advantageously be carried out with a spectrophotometer with the sensing beam placed in the formulation, the absorption of radiation in the ultraviolet range (UV) being proportional to the HA concentration. A particularly advantageous feature of this invention is that it obviates the need to mix exact quantities of water and hyaluronic acid to obtain the specified concentration and ensure that such concentration is maintained through the process. Instead, the initial HA and water mix has an approximate concentration lower than the final formulation, thus simplifying the process.

The vacuum applied during the concentrating process is preferably less than 200 millibars absolute pressure, in particular in the range of 30 to 60 millibars, for example 40 millibars, whereby the boiling temperature is around 26 to 280° C. Industrial equipment is economical to operate reliably at such pressures, and the low temperature avoids any significant or measurable reduction of the hyaluronic acid molecular weight.

The filter pore size is advantageously around 0.22 μm or less, thus ensuring the preparation of a highly sterile formulation. Filter sterilized ready-to-use high viscosity pharmaceutical formulation with HA concentration in the range of 1 to 3% can thus advantageously be prepared in a sterile and economical manner, according to this invention.

Figure 2:
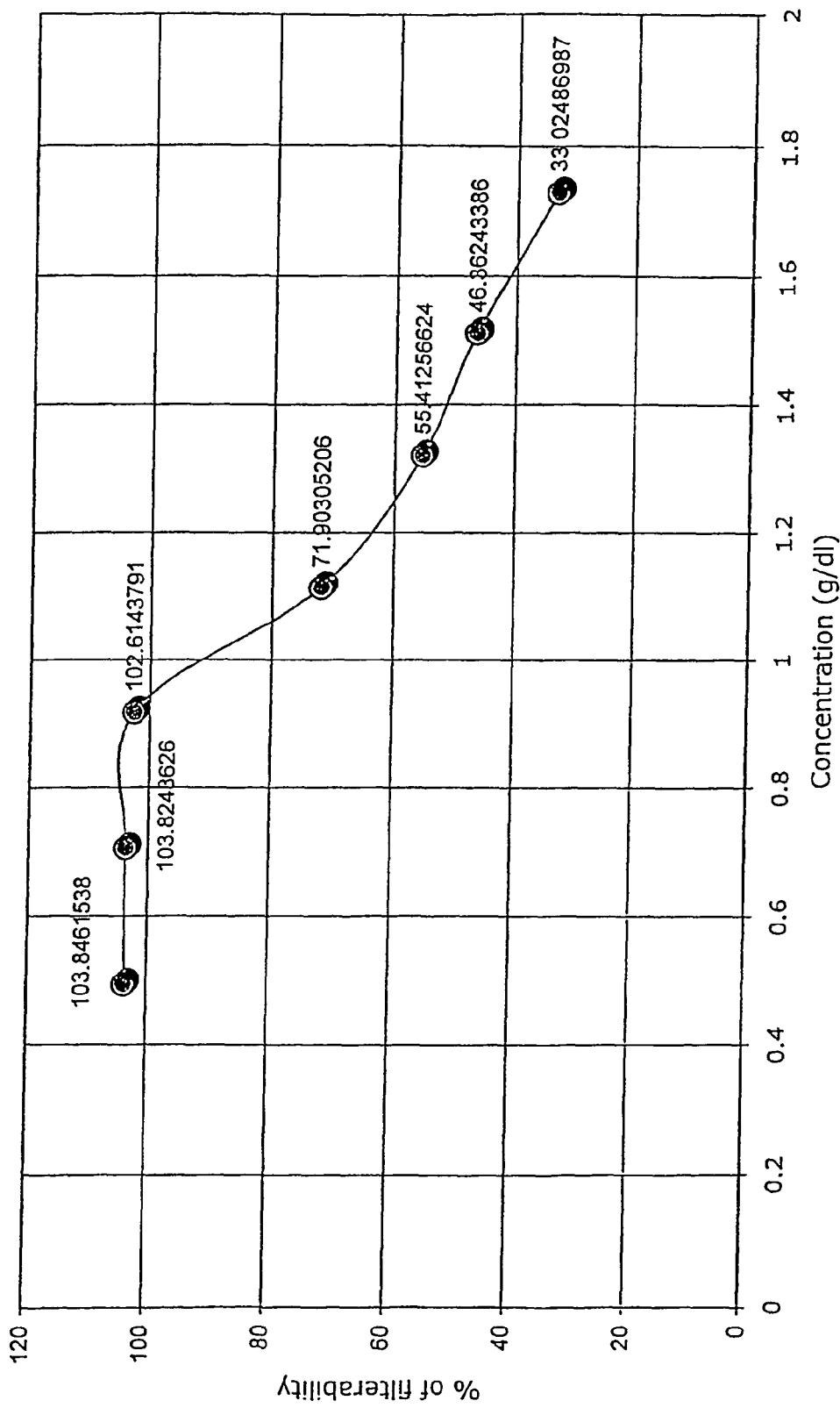
Figure 3:
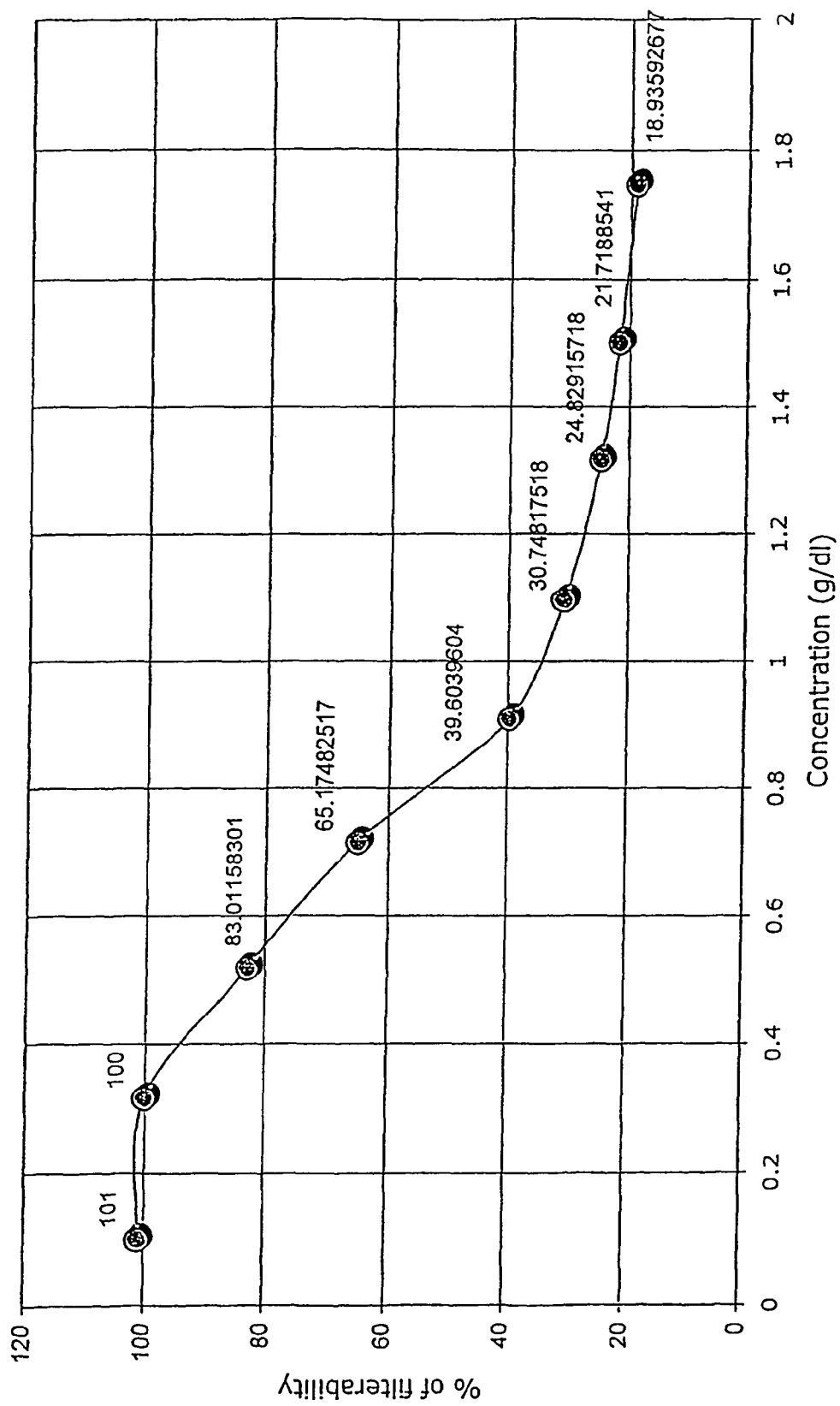
Figure 4:
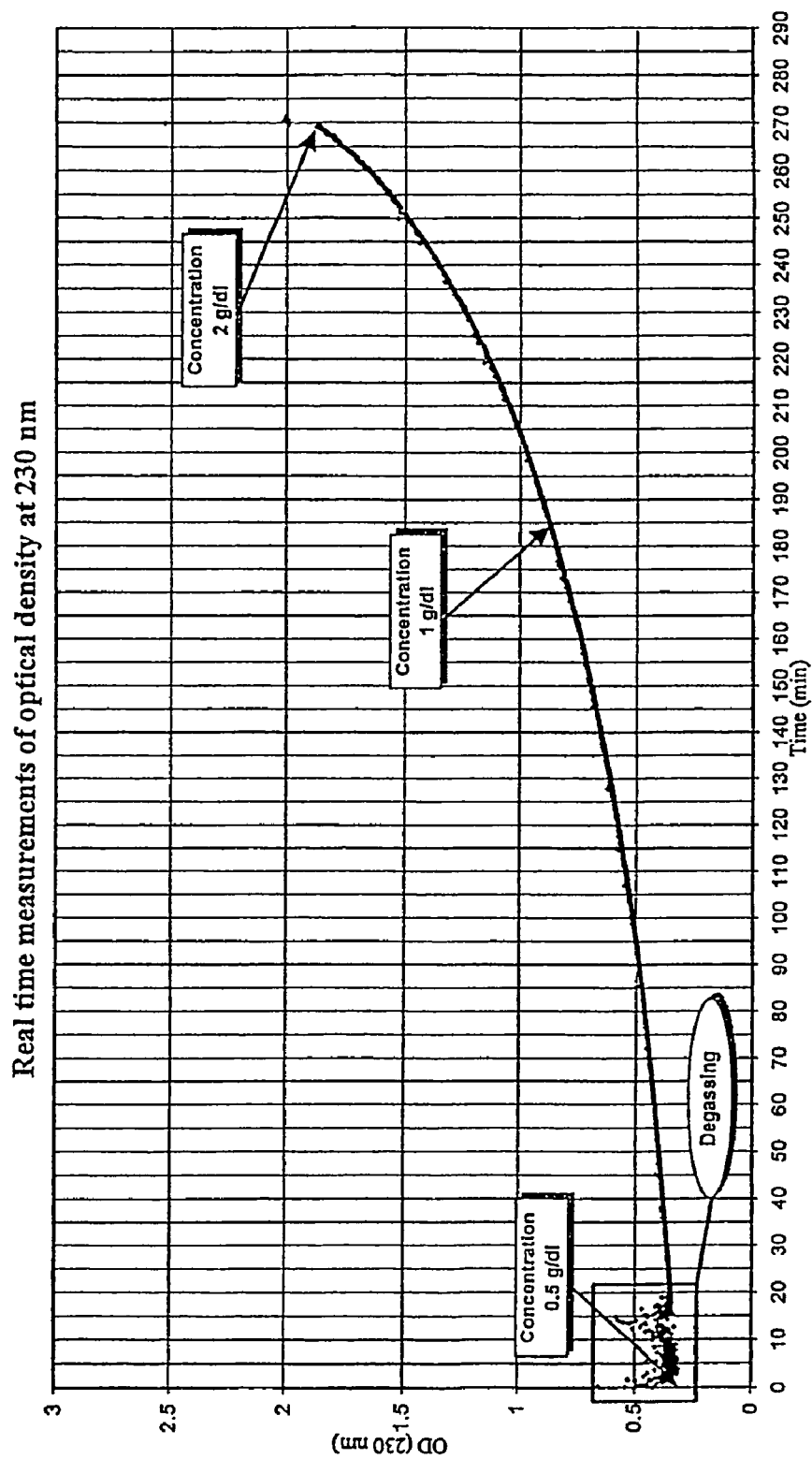

Further advantageous aspects of this invention will be apparent from the claims and the following detailed description of an example of a process and annexed drawing in which:

FIG. 1 represents a flow chart illustrating steps in an embodiment of the process according to the invention;

FIGS. 2 and 3 are graphs represent the percentage of HA of molecular weight 1.1 million and 2.2 million Daltons, respectively, passing through a filter of 0.22 μm as a function of the % w/v concentration in an aqueous solution, at 20° C. and neutral pH;

FIG. 4 is a graph representing the optical density (OD) at 230 nm of the formulation as a function of time during the concentration process as measured by a spectrophotometer.

Referring to FIG. 1, a process for preparing a ready-to-use aqueous pharmaceutical formulation comprising a high molecular weight hyaluronic acid salt at a specified pharmaceutical concentration is shown. Prior to preparing the formulation, the process plant equipment is cleaned with purified water (step 1), sterilized with clean steam (step 2), and washed with sterile distilled water for injection (WFI) (step 3).

A preparation of an aqueous HA formulation, for example a diluted sodium hyaluronate solution at a concentration less than the concentration specified for the final pharmaceutical formulation is introduced into a mixing reactor for preparing the prefiltered formulation (step 4).

The aqueous HA solution may either be prepared from a dried HA salt or from the solution prepared according to PCT application WO 00/44925, before the drying process.

The addition of a concentrated salt solution (25×), dosed by a peristaltic pump, is carried out in order to add the right amount of salts coupled with the amount of HA added (step 5). The salt solution normally contains NaCl, buffers and other excipients specified for the final pharmaceutical formulation, and they are added in order to bring the pH to a physiological pH, such as 7.4, and to give the final formulation the physiological osmolarity, such as 300 mOsm/lt.

The salt solution, buffers and other excipients may also be added aseptically after the filtration step 7 directly into the reaction chamber. This is particularly advantageous for very high molecular weight HA in view of the fact that salts decrease the filterability of HA and thus would require greater dilution of the pre-filtered solution. The amount of excipients added can be monitored in real time by an electrical conductivity sensor (probe) in the reaction chamber. The conductivity of the HA formulation is related to the amount of excipient in the formulation and can be determined empirically. Thus, by measuring the conductivity of the HA formulation as excipient is added in the reaction chamber until the required concentration is reached, the required amount of excipient in the formulation can be added in a simple, reliable and precise manner. The aforegoing in particular obviates the need to calculate and measure dosages in advance, and in particular removes the problem of having to take into account and compensate for the certain amount of HA, even if small, retained by the filter during the filtration step 7.

By way of example, the formulation may be prepared from 45 grams of dried sodium hyaluronate of an average molecular weight of 2.2 million Daltons mixed with 15 liters of WFI. In this case, due to the high molecular weight of HA, the salts and buffer solution is added after filtration in order to avoid a greater dilution of the pre-filtered solution than needed, as mentioned above.

A stirring machine in the reactor mixes the prefiltered solution (step 6), for example for about 120 minutes, until it is homogeneous. In this particular example, the prefiltered solution has an HA concentration of 0.3% wt/v. At this concentration, hyaluronic acid with a molecular weight of 2.2 million Daltons, at room temperature and physiological pH, has a low viscosity which enables it to pass entirely through a filter with pore size of 0.22 µm. The maximum viscosity at which all of the HA formulation passes through a filter having a pore size of 0.22 µm, is found to be approximately 5 Pa·s as measured at $0.1 \text{ s}^{-1}$ shear rate at 20° C. This maximum viscosity however will depend on the filter pore size: a smaller pore size, such as 0.1 µm, would lower this maximum viscosity at which all HA would pass through the filter.

As discussed above, the maximum concentration of HA in an aqueous solution at which substantially all the HA will pass through a sterilizing filter, for example a filter of 0.22 µm, will depend on the molecular weight of the hyaluronic acid. This may be shown with reference to the graphs shown in FIGS. 2 and 3, whereby FIG. 2 shows the percentage of sodium hyaluronate at average molecular weight of about 1.1 million Daltons passing through a filter of 0.22 µm pore size at substantially ambient temperature (around 20° C.) and substantially neutral pH (around 7) as a function of the concentration (grams of sodium hyaluronate per deciliter of water % wt/v).

FIG. 3 shows a similar graph under the same conditions except that the sodium hyaluronate has an average molecular weight of about 2.2 million Daltons. It may be seen on the graph of FIG. 2 that all the sodium hyaluronate at a molecular weight of 1.1 million Daltons passes through the filter up to a concentration of about 0.92% wt/v (or g/dl), whereas for sodium hyaluronate having a molecular weight of 2:2 million Daltons, the maximum concentration is approximately 0.32% wt/v. Therefore, as the molecular weight of the hyaluronic acid salt increases from 1.1 to 2.2 million Daltons, the maximum concentration of HA in an aqueous solution to pass 100% through the 0.22 µm filter will decrease from about 0.94% wt/v to about 0.32% wt/v.

In an industrial process, and considering that after filtration the solution is concentrated, it is preferred to have a concentration somewhat lower than the upper limit to ensure that the filtering process is complete and reliable with a certain margin for error or variations from batch to batch in the molecular weight of the sodium hyaluronate, the temperature, and the mixing concentrations.

The solution may be forced through the sterilizing filter (step 7) by introducing a gas under pressure, such a nitrogen, for example at around 3 bars pressure in the mixing reactor, or by means of a pump. The sterilizing filter preferably has a pore size of 0.22 µm, but filters having other pore sizes less than 0.45 µm and greater than around 0.1 µm, may also be used to the extent such filters are or become commercially available.

When all the solution has passed through the filter into a distiller, the distiller is sealed off from the filter and mixing reactor with a valve, and a vacuum pump is activated and regulates the pressure in the distiller by means of a regulatory valve (steps 8, 9, 10). The pressure is less than 200 millibars in order to bring the boiling temperature below 60° C., but preferably the pressure is in the region of 30 to 60 millibars, for example at 40 millibars, whereby the boiling temperature of water is in the region of 26 to 28° C., close to ambient temperature.

Instead of the distiller, a thin film evaporator or any other under-vacuum concentrators can be useful for a batch, fed-batch or continuous concentration of the HA formulation.

A heating jacket around the distiller supplies heat energy during the boiling process. Advantageously, the boiling temperature of less than 30° C. ensures that there is essentially no degradation of the hyaluronic acid such that the molecular weight of the hyaluronic acid is not reduced.

An HA concentration sensor, advantageously in the form of a spectrophotometer having an optical fibre immersed in the formulation, may be provided to measure in real time the concentration of hyaluronic acid (step 11) and automatically stops the boiling process when the specified concentration is reached. The spectrophotometer may for example be based on the absorption of a beam of ultraviolet light (e.g. wave length 230 nm) positioned within the solution in the distiller. FIG. 4 shows the optical density at 230 nm measured over time during the whole concentration process (for example up to 2% w/v.) The real time HA concentration measurement obviates the need to mix very precise quantities during the preparation of the diluted prefiltered solution, thus simplifying the process.

The vacuum boiling also has an important advantage of degassing the formulation which, in view of the mixing process and application of nitrogen at high pressure during the filtering process, comprises bubbles, microbubbles and dissolved gas that are not acceptable in the final pharmaceutical formulation.

When the HA concentration sensor in the distiller signals that the specified concentration is attained, the pressure in the distiller is rapidly increased by introducing gas, for example nitrogen, therein (step 13) and the jacket heating around the distiller is cooled to ambient temperature or less, thus immediately stopping the concentration process of the formulation (step 12).

It may be noted that with a process according to this invention, the concentration of hyaluronic acid in the formulation may be in the range up to 3%, depending on the specified pharmaceutical use.

The formulation can then be pumped or pushed by a gas (e.g. nitrogen) under pressure into sterile tanks (steps 28, 30) for filling at another location and/or in a subsequent stage directly into sterile recipients, such as syringes (step 16), ready for use. The pharmaceutical formulation may also be directly filled into sterile recipients for pharmaceutical use without intermediate storage in a sterile tank.

The invention claimed is:

1. A process for preparing a sterile ready-to-use aqueous pharmaceutical formulation comprising a high molecular weight hyaluronic acid salt (HA) at a specified concentration, comprising the steps of:

providing an aqueous formulation comprising high molecular weight HA at a concentration of less than the specified concentration;

passing said aqueous formulation through a filter having a pore size less than 0.45 μm; and greater than 0.1 μm;

concentrating said aqueous formulation by applying a vacuum and boiling off water until said specified concentration is reached; and after the concentration step, filling the pharmaceutical formulation directly into sterile recipients ready for pharmaceutical use, or into sterile tanks and subsequently directly into sterile recipients ready for pharmaceutical use.

2. Process according to claim 1, wherein the vacuum is at a pressure in the range of 30 to 60 millibars.

3. Process according to claim 1, wherein the average molecular weight of HA is in the range of 800,000 to 5,000,000 Daltons.

4. Process according to claim 1, wherein the filter has a pore size in the range of 0.22 μm to 0.1 μm.

5. Process according to claim 1, wherein, during the concentration step, the concentration of HA is measured in real time and the vacuum boiling process is stopped automatically when the specified concentration is measured.

6. Process according to claim 1, wherein the HA concentration is measured with a spectrophotometer sensing wave radiation absorption in the formulation.

7. Process according to claim 1, wherein excipients are added to the formulation after the filtration step, and wherein the conductivity of the HA formulation is measured in real time until the amount of excipients reaches a required value.

* * * * *